United States Patent [19]

Phelps et al.

[11] Patent Number: 5,142,088
[45] Date of Patent: Aug. 25, 1992

[54] PREPARATION OF BRANCHED POLYCARBONATES AND CHLOROFORMATES, AND INTERMEDIATES THEREFOR

[75] Inventors: Peter D. Phelps, Schenectady; Eugene P. Boden, Scotia, both of N.Y.; Paul W. Buckley, Mt. Vernon, Ind.

[73] Assignee: General Electric Company, Schenectady, N.Y.

[21] Appl. No.: 646,590

[22] Filed: Jan. 28, 1991

[51] Int. Cl.$^5$ .................. C07C 68/02; C07C 69/96; C07C 69/17
[52] U.S. Cl. .............................. 558/281; 528/372; 558/260; 558/265; 560/80; 560/85; 560/86
[58] Field of Search .................. 560/86, 85, 80; 558/265, 281, 260

[56] References Cited

U.S. PATENT DOCUMENTS 4,001,184 1/1977 Scott ................... 558/265

Primary Examiner—Jose G. Dees
Assistant Examiner—Vera C. Clarke
Attorney, Agent, or Firm—William H. Pittman; James C. Davis, Jr.

[57] ABSTRACT

Ester polyphenols such as the tris(bisphenol A) ester of trimellitic acid are prepared by the reaction of the corresponding aromatic poly(acyl halide) with a dihydroxyaromatic compound such as bisphenol A. They may be employed in the preparation of branched polycarbonates via chloroformate oligomer compositions.

25 Claims, No Drawings

PREPARATION OF BRANCHED POLYCARBONATES AND CHLOROFORMATES, AND INTERMEDIATES THEREFOR

This invention relates to the preparation of branched polycarbonates, and more particularly to novel intermediates useful in said preparation and a method for conversion of said intermediates via chloroformate oligomers to said branched polycarbonates.

Branched polycarbonates are known to be superior to conventional linear polycarbonates for some purposes. For example, the melt viscosity properties of branched polycarbonates are superior to those of linear polycarbonates for such operations as blow molding, which involves the formation of a hollow parison which hangs from the nozzle and is shaped by a mold into the desired object.

One method of forming branched polycarbonates, disclosed, for example, in U.S. Pat. No. 4,001,884, involves the incorporation of an aromatic polycarboxylic acid or functional derivative thereof in a conventional polycarbonate-forming reaction mixture. The examples of said patent demonstrate such incorporation in a reaction in which phosgene undergoes reaction with a bisphenol, under alkaline conditions typically involving a pH above 10. Experience has shown that a preferred aromatic polycarboxylic acid derivative is trimellitic acid trichloride. Also disclosed in the aforementioned patent is the employment of a monohydric phenol as a molecular weight regulator; it functions as a chain termination agent by reacting with chloroformate groups on the forming polycarbonate chain.

It has more recently been recognized that the presence of diaryl carbonates, as a result of reaction of phosgene with the monohydric phenols used as chain termination agents, can cause numerous problems in polycarbonate molding operations. These may include difficulties in removing molded polycarbonate articles from the mold, in producing parts using rapid cycle times and in producing parts without physically or optically flawed surfaces.

The presence of diaryl carbonates has been found particularly vexatious in blow molding operations. In addition to plate-out, vaporization and the other problems identified above, the diaryl carbonates tend to block vents in the mold.

A number of patents, including U.S. Pat. Nos. 4,737,573, 4,743,676 and 4,973,664, disclose methods for preparing polycarbonates from chloroformate oligomers typically comprising mono- and/or bischloroformates. Such methods materially decrease the proportion of diaryl carbonate in the polycarbonate product. This is true because the monohydric phenol employed as chain termination agent is not introduced into the reaction mixture until the chloroformate composition has been prepared, at which time unreacted phosgene has ordinarily been purged from the system and further addition of phosgene is unnecessary.

Incorporation of the aforementioned branching agents in polycarbonate-forming reactions from chloroformate oligomers has generally not proved successful. A branching reaction between a phenolic species (i.e., a dihydroxyaromatic compound or hydroxy-terminated polycarbonate, usually oligomeric) and a branching reagent such as trimellitic acid trichloride requires a relatively high pH, typically in the range of about 10-12. On the other hand, the chloroformate-forming reaction requires a lower pH, most often below 10, at which incorporation of the branching agent is incomplete. If the aromatic polycarboxylic acid derivative is introduced during conversion of the chloroformate composition to polycarbonate, its low reactivity compared with that of chloroformates results in little if any branching.

Accordingly, interest continues in developing methods for preparing relatively diaryl carbonate-free branched polycarbonate. Such a method, and intermediates useful therein, are provided by the present invention.

In one of its aspects, the invention includes ester polyphenols having the formula $$A^1 \left( \overset{O}{\underset{\|}{C}}-O-A^2-OH \right)_p. \quad (I)$$

wherein $A^1$ is a tri- or tetravalent aromatic radical, $A^2$ is a divalent aromatic radical and p is 3 or 4.

The $A^1$ radicals in the ester polyphenols of this invention may be trivalent or tetravalent and may contain any number of rings, either fused or linked if more than one ring is present. Other than the ester phenol moieties thereon, they may be unsubstituted or substituted, any substituents being substantially inert under the conditions of the invention including those of formation of the ester polyphenol and chloroformate composition and polycarbonate preparation therefrom. Illustrative substituents include halo, nitro, hydroxy and alkoxy. The $C_{6-10}$ aromatic hydrocarbon radicals are generally preferred, with monocyclic radicals being particularly preferred. Most preferred are compounds in which p is 3, especially derivatives of trimellitic acid (1,2,4-benzenetricarboxylic acid) in which $A^1$ is

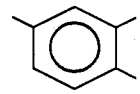

The $A^2$ radicals may be aromatic hydrocarbon or substituted aromatic hydrocarbon radicals, with illustrative substituents being alkyl, cycloalkyl, alkenyl (e.g., crosslinkable-graftable moieties such as allyl), halo (especially fluoro, chloro and/or bromo), nitro and alkoxy.

Preferably, the $A^2$ values have the formula $-A^3-Y-A^4-$, wherein each of $A^3$ and $A^4$ is a monocyclic divalent aromatic radical and Y is a bridging radical in which one or two atoms separate $A^3$ from $A^4$. The free valence bonds are usually in the meta or para positions of $A^3$ and $A^4$ in relation to Y.

The $A^3$ and $A^4$ values may be unsubstituted phenylene or substituted derivatives thereof wherein the substituents are as defined for $A^2$. Unsubstituted phenylene radicals are preferred. Both $A^3$ and $A^4$ are preferably p-phenylene, although both may be o- or m-phenylene or one o- or m-phenylene and the other p-phenylene.

The bridging radical, Y, is one in which one or two atoms, preferably one, separate $A^3$ from $A^4$. It is most often a hydrocarbon radical and particularly a saturated $C_{1-12}$ aliphatic or alicyclic radical such as methylene, cyclohexylmethylene, [2.2.1]bicycloheptylmethylene, ethylene, ethylidene, 2,2-propylidene, 1,1-(2,2-dimethylpropylidene), cyclohexylidene, cyclopentadecylidene, cyclododecylidene or 2,2-adamantylidene, especially an alkylidene radical. Aryl-substituted radicals are included, as are unsaturated radicals and radicals containing atoms other than carbon and hydrogen; e.g., oxy groups. Substituents such as those previously enumerated may be present on the aliphatic, alicyclic and aromatic portions of the Y group. Most preferably, each of $A^3$ and $A^4$ is p-phenylene and Y is isopropylidene.

The preferred ester polyphenol of the present invention is the tris(bisphenol A) ester of trimellitic acid, having the formula

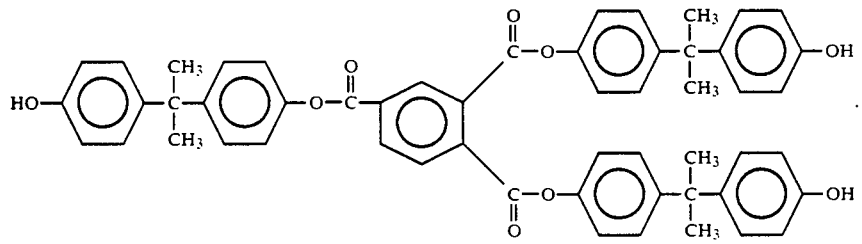

It might be expected that the ester polyphenols of this invention would have been formed, at least in small amounts, upon addition of a poly(acyl halide) such as trimellitic acid trichloride to an interfacial reaction mixture comprising bisphenol and phosgene. However, the high reactivity of the bisphenol with the phosgene under the prevailing reaction conditions result in essentially complete conversion of any phenolic hydroxy groups to chloroformates. Hence, ester polyphenols are not formed.

Another aspect of the present invention is a method for preparing a branched chloroformate oligomer composition which comprises:

(A) contacting, under reactive conditions and in the presence of a catalytic amount of at least one trialkylamine, an aromatic poly(acyl halide) of the formula

(II)

wherein X is chlorine or bromine, with at least one dihydroxyaromatic compound of the formula $A^2(OH)_2$ (hereinafter sometimes "bisphenol") in a reaction system comprising water and a substantially inert, substantially water-insoluble organic liquid, the pH of the aqueous phase of said reaction system being in the range of about 10-12 and the proportion of said aromatic poly(acyl halide), based on said dihydroxyaromatic compound, being in the range of about 0.1-1.0 mole percent, to form a composition comprising at least one ester polyphenol of formula I; and (B) reducing the pH of the reaction system to a valve below that of step A and in the range of about 7-10, and introducing phosgene into said system.

For the most part, the proportions of reagents employed in this method are such as to produce compositions comprising principally molecules in which all end groups are chloroformate groups; i.e., molecules corresponding to linear bischloroformates. It is within the scope of the invention to employ compositions comprising molecules containing one or more terminal hydroxy groups, corresponding to the monochloroformates disclosed and claimed in copending, commonly owned application Ser. No. 07/519,980, now abandoned.

The aromatic poly(acyl halides) of formula II employed for preparation of branched chloroformate oligomer compositions may be chlorides or bromides. The chlorides are preferred because of their availability and relatively low cost. Particularly preferred is trimellitic acid trichloride.

The reaction which forms the branched chloroformate composition takes place in a reaction system comprising water and a substantially inert, substantially water-insoluble organic liquid. Illustrative organic liquids are aliphatic hydrocarbons such as hexane and n-heptane; chlorinated aliphatic hydrocarbons such as methylene chloride, chloroform, dichloroethane, trichloroethane, tetrachloroethane, dichloropropane and 1,2-dichloroethylene; aromatic hydrocarbons such as toluene and xylene; substituted aromatic hydrocarbons such as chlorobenzene, o-dichlorobenzene, the chlorotoluenes, nitrobenzene and acetophenone; and carbon disulfide. The chlorinated aliphatic hydrocarbons, especially methylene chloride, are preferred.

Step A is conducted at a pH in the range of about 10-12, typically provided by the introduction of aqueous base into the reaction system. The employment of aqueous alkali metal hydroxide solutions such as sodium hydroxide or potassium hydroxide is preferred, with sodium hydroxide being particularly preferred by reason of its availability and low cost. Reaction temperatures are usually in the range of about 10°-50° C.

A catalytic amount of at least one trialkylamine is incorporated in the reaction mixture of step A, to catalyze the reaction of the aromatic poly(acyl halide) with the bisphenol. Illustrative trialkylamines are triethylamine, tri-n-propylamine, diethyl-n-propylamine and tri-n-butylamine, with triethylamine being preferred. The proportion thereof is generally about 50-100 ppm. based on the organic liquid.

The product of step A is an ester polyphenol of formula I; i.e., an ester polyphenol of the present invention. Although it may be isolated if desired, isolation is usually not necessary. It may be employed as a branching agent in a conventional interfacial phosgenation reaction to form a branched polycarbonate. Preferably, however, it is converted in step B to a branched chloroformate oligomer composition.

In said step, the ester polyphenol and bisphenol are phosgenated to form the branched chloroformate oligomer composition. Phosgenation takes place at a pH below that of step A and in the range of about 7-10 and preferably about 7.5-8.5. Reaction temperatures are generally in the range of about 15°-50° C., and other conditions are conventional for chloroformate preparation.

The proportion of poly(acyl halide) present during step B is about 0.1-1.0 mole percent, based on bisphenol. The preferred amount is about 0.3-0.5 mole percent, since greater amounts can result in some degree of crosslinking in addition to branching.

In accordance with copending, commonly owned application Ser. No. 07/331,787, it is often preferred to employ at least one trialkylamine in step B, in the amount of about 50-100 ppm. based on the organic liquid. This is the same amount employed in step A, and is is usually not necessary to adjust the trialkylamine concentration between steps A and B. The presence of trialkylamine in this step permits employment of recycled organic liquid, previously used for polycarbonate preparation. It also frequently decreases the amount of phosgene required and the amount of unreacted phenolic compounds in the product, and increases the degree of polymerization of the chloroformate oligomer composition.

Although it is possible to isolate the chloroformate oligomer composition prior to conducting step C as described hereinafter, isolation is not necessary and is usually not preferred.

Branched chloroformate oligomers prepared by the method comprising steps A and B are another aspect of the invention. In addition to the branched chloroformates, they may contain linear mono- and bischloroformates prepared by identical reactions which do not incorporate the ester polyphenol. Said compositions may be converted to branched polycarbonates by treatment with a trialkylamine at a pH in the range of about 10-14. Accordingly, still another aspect of the invention is a method for preparing a substantially diaryl carbonate-free branched polycarbonate which comprises conducting steps A and B as described hereinabove, and (C) adding an effective amount for polycarbonate formation of at least one trialkylamine and increasing the pH to a value in the range of about 10-14.

The trialkylamines employed in step C are generally selected from the same class as those employed in step B, and in fact the same trialkylamine may be employed. However, while trialkylamine presence in step B is optional and it is present, if at all, only in relatively small amounts, its presence in somewhat larger amounts is required in step C. The proportion thereof is typically in the range of about 0.025-3.0 mole percent based on total chloroformate oligomer.

It is within the scope of the invention to incorporate in the reaction mixture for step C at least one monohydroxyaromatic compound or salt thereof, as a polycarbonate chain termination agent. Reference is made, for example, to U.S. Pat. No. 4,743,676, the disclosure of which is incorporated by reference herein. Suitable compounds for this purpose are phenol, p-t-butylphenol, p-cumylphenol, octylphenol and nonylphenol; phenol is often preferred by reason of its low cost, availability and effectiveness. The concentration of chain termination agent is typically about 0.5-7.0 mole percent, based on structural units in the chloroformate composition.

Other conditions in step C are conventional for polycarbonate formation from bischloroformate oligomers. They include temperatures in the range of about 0°-100° C. and preferably about 25°-50° C., and pH values in the range of about 10-14 and preferably about 10.5-12.5. If not introduced after step B, a chain termination agent may be added during step C.

The required pH values are most often achieved by the addition of further aqueous base. Said base may be an alkali metal hydroxide, often the same one employed in steps A and B. It is also within the scope of the invention, however, to employ an alkaline earth metal base such as calcium hydroxide, which provides a buffered pH in the range of about 12-13 as described in U.S. Pat. No. 4,973,664.

Following polycarbonate preparation in step C, the polycarbonate may be recovered by conventional procedures. These typically include precipitation by a nonsolvent such as methanol or by steam precipitation. Further recovery operations such as filtration or decantation may be employed as necessary.

The invention is illustrated by the following examples.

EXAMPLE 1

A 1-liter 5-necked Morton flask equipped with a condenser containing solid carbon dioxide, a pH electrode, a caustic addition port, a mechanical stirrer and a phosgene dip tube was charged with 93 grams (408 mmol.) of bisphenol A, 550 ml. of methylene chloride, 250 ml. of water, 30 mg. (0.3 mmol.) of triethylamine, 3 ml. of 50% aqueous sodium hydroxide solution and 75 mg. of 2,4-dimethylbenzophenone as an internal standard. The mixture was stirred as a solution of 465 mg. (1.8 mmol.) of trimellitic acid trichloride in 5 ml. of methylene chloride was added over 5 minutes. Stirring was continued for 10 minutes, after which a 3-4 ml. sample was removed, quenched in aqueous hydrochloric acid solution and analyzed by high pressure liquid chromatography; it was found to contain greater than 90% of the theoretical amount of the desired tris(bisphenol A) ester of trimellitic acid.

The reaction mixture was phosgenated for 15 minutes at 3 grams/minute of phosgene, while the pH was maintained in the range of 7.5-8.2 by addition of aqueous sodium hydroxide solution. There was then added 1.34 grams (14 mmol.) of phenol and the pH was adjusted to 10.2 by addition of further base. Triethylamine, 300 mg. (3.0 mmol.), was added and the pH was maintained at 10.2-10.5 for 15 minutes. To ensure complete polymerization, additional phosgene was added in the amount of 6 grams.

The mixture was separated into aqueous and organic layers and the organic layer was washed with aqueous hydrochloric acid solution and twice with water. The desired branched polycarbonate was isolated by addition of excess methanol in a blender, followed by filtration and drying.

EXAMPLE 2

A mixture of 2.27 kg. (9.96 moles) of bisphenol A, 6.8 liters of methylene chloride, 3.1 liters of water and 0.5 ml. (5 mmol.) of triethylamine was charged to a 35-liter glass reactor and the pH was adjusted to 10.5 by the addition of 50% aqueous sodium hydroxide solution. A solution of 11.32 grams (42 mmol.) of trimellitic acid trichloride in 500 ml. of methylene chloride was added over 5 minutes and the mixture was stirred for 2-3 minutes, to form the desired tris(bisphenol A) ester.

Phosgene was introduced over 22 minutes to a total of 1100 grams while the pH was maintained at 8.2-8.5, followed by 32.25 grams (343 mmol.) of phenol as a solution in 2.1 liters of water. The pH was raised to 10.5 by the addition of further base and stirring was continued for 15 minutes, after which an additional 250 grams of phosgene was added to ensure complete polymerization. The organic layer was separated and washed twice with aqueous hydrochloric acid solution and five times with water, after which the desired branched polycarbonate was isolated by steam precipitation and dried. It was found to have a melt index ratio of 2.6 and a complex viscosity ratio of 2.9, and no diphenyl carbonate could be detected.

What is claimed is:

1. An ester polyphenol having the formula

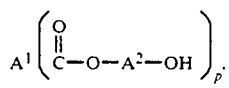
(I)

wherein $A^1$ is a tri- or tetravalent aromatic radical, $A^2$ is a divalent aromatic radical and p is 3 or 4.

2. An ester polyphenol according to claim 1 wherein p is 3.

3. An ester polyphenol according to claim 2 wherein $A^2$ has the formula

wherein each of $A^3$ and $A^4$ is a monocyclic divalent aromatic radical and Y is a bridging radical in which one or two atoms separate $A^3$ from $A^4$.

4. An ester polyphenol according to claim 3 wherein $A^1$ is

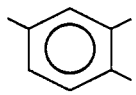

5. An ester polyphenol according to claim 4 wherein each of $A^3$ and $A^4$ is p-phenylene and Y is isopropylidene.

6. A method for preparing a branched chloroformate oligomer composition which comprises:

(A) contacting, at a temperature in the range of about 10°-50° C. and in the presence of a catalytic amount of at least one trialkylamine, an aromatic poly(acyl halide) of the formula

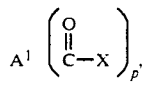
(II)

wherein X is chlorine or bromine and p is 3 or 4, with at least one dihydroxyaromatic compound of the formula $A^2(OH)_2$, wherein $A^2$ is a divalent aromatic radical, in a reaction system comprising water and a substantially inert, substantially water-insoluble organic liquid, the pH of the aqueous phase of said reaction system being in the range of about 10-12 and the proportion of said aromatic poly(acyl halide), based on said dihydroxyaromatic compound, being in the range of about 0.1-1.0 mole percent, to form a composition comprising at least one ester polyphenol of the formula

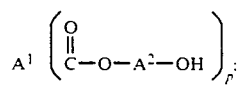
(I)

(B) reducing the pH of the reaction system to a value below that of step A and in the range of about 7-10, and introducing phosgene into said system.

7. A method according to claim 6 wherein X is chlorine.

8. A method according to claim 7 wherein p is 3 and $A^1$ is

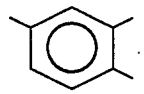

9. A method according to claim 8 wherein the organic liquid is methylene chloride.

10. A method according to claim 9 wherein the proportion of trialkylamine is about 50-100 ppm. based on the organic liquid.

11. A method according to claim 10 wherein said trialkylamine is also present in step B.

12. A method according to claim 11 wherein the trialkylamine employed in steps A and B is triethylamine.

13. A method according to claim 8 wherein $A^2$ has the formula

wherein each of $A^3$ and $A^4$ is a monocyclic divalent aromatic radical and Y is a bridging radical in which one or two atoms separate $A^3$ from $A^4$.

14. A method according to claim 13 wherein each of $A^3$ and $A^4$ is p-phenylene and Y is isopropylidene.

15. A branched chloroformate oligomer composition prepared by the method of claim 6.

16. A branched chloroformate oligomer composition prepared by the method of claim 8.

17. A branched chloroformate oligomer composition prepared by the method of claim 14.

18. A method for preparing a branched chloroformate oligomer composition which comprises:

(A) contacting, at a temperature in the range of about 10°-50° C. and in the presence of a catalytic amount of at least one trialkylamine, an aromatic poly(acyl halide) of the formula

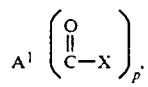
(II)

wherein X is chlorine or bromine, with at least one dihydroxyaromatic compound of the formula $A^2(OH)_2$, wherein $A^2$ is a divalent aromatic radical and p is 3 or 4, in a reaction system comprising water and a substantially inert, substantially water-insoluble organic liquid, the pH of the aqueous phase of said reaction system being in the range of about 10-12 and the proportion of said aromatic poly(acyl halide), based on said dihydroxyaromatic compound, being in the range of about 0.3-0.5 mole percent, to form a composition comprising at least one ester polyphenol of the formula

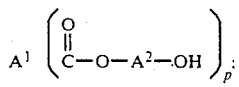 (1)

(B) reducing the pH of the reaction system to a value below that of step A and in the range of about 7-10, and introducing phosgene into said system; and (C) adding an effective amount for polycarbonate formation of at least one trialkylamine and increasing the pH to a value in the range of about 10-14.

19. A method according to claim 18 wherein X is chlorine.

20. A method according to claim 19 wherein p is 3 and $A^1$ is

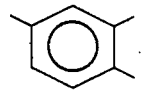

21. A method according to claim 20 wherein the organic liquid is methylene chloride.

22. A method according to claim 21 wherein a trialkylamine is also present in steps B and C in the amount of about 50-100 ppm. based on the organic liquid. trialkylamine employed in steps A, B and C is triethylamine.

23. A method according to claim 22 wherein the trialkylamine employed in steps A, B and C is triethylamine.

24. A method according to claim 20 wherein $A^2$ has the formula $$-A^3-Y-A^4,$$

wherein each of $A^3$ and $A^4$ is a monocyclic divalent aromatic radical and Y is a bridging radical in which one or two atoms separate $A^3$ from $A^4$.

25. A method according to claim 24 wherein each of $A^3$ and $A^4$ is p-phenylene and Y is isopropylidene.

* * * * *